United States Patent [19]

Reverman

[11] Patent Number: 4,757,008

[45] Date of Patent: Jul. 12, 1988

[54] ENZYME IMMOBILIZATION IN A MACROPOROUS NON-IONIC RESIN

[75] Inventor: Lawrence F. Reverman, Elkhart, Ind.

[73] Assignee: Miles Inc., Elkhart, Ind.

[21] Appl. No.: 831,860

[22] Filed: Feb. 24, 1986

[51] Int. Cl.⁴ .............. C12P 19/24; C12N 11/08; C12N 11/06; C12N 11/04

[52] U.S. Cl. .................... 435/94; 435/180; 435/181; 435/182

[58] Field of Search .............. 435/174, 176, 177, 180, 435/181, 182, 94

[56] References Cited

U.S. PATENT DOCUMENTS

| | | | |
|---|---|---|---|
| 3,705,084 | 12/1972 | Reynolds | 435/180 |
| 3,788,945 | 1/1974 | Thompson et al. | 435/94 |
| 3,960,663 | 6/1976 | Tamura et al. | 435/180 |
| 4,001,085 | 1/1977 | Keyes | 435/174 |
| 4,078,970 | 3/1978 | Fujita et al. | 435/180 |
| 4,323,650 | 4/1982 | Rosevear | 435/174 |
| 4,504,582 | 3/1985 | Swann | 435/181 X |

*Primary Examiner*—David M. Naff
*Attorney, Agent, or Firm*—Jerome L. Jeffers

[57] ABSTRACT

Enzyme-containing microbial cells are contacted with a macro-porous non-ionic resin under reduced pressure below atmospheric to cause the cells to become incorporated into pores of the resin. The resin is then contacted with a multi-functional, amine reactive material to immobilize the cells within the pores. Prior to contacting with the resin, cells may be disrupted to produce a system containing cell fragments, intact cells and solubilized enzyme. A preferred enzyme is glucose isomerase.

13 Claims, No Drawings

ENZYME IMMOBILIZATION IN A MACROPOROUS NON-IONIC RESIN

The present invention involves an enzyme-containing cell immobilized conjugate and a method of preparing such a conjugate. In the preferred embodiment, glucose isomerase producing cells are immobilized on a support of non-ionic resin.

BACKGROUND OF THE INVENTION

Enzymes are biologically active proteins that catalyze certain reactions. Enzymes are useful in many industrial and research applications, such as fermentation, food processing, and medical research.

Since enzymes are commonly water soluble as well as being generally unstable, they are subject to deactivation and are difficult to remove for re-use from aqueous solutions in which they are utilized. These difficulties have led to an increased cost in the use of enzymes in commercial scale operations due to the necessity for their frequent replacement. In order to reduce the high cost of enzyme replacement, various methods to immobilize enzymes or enzyme-producing cells prior to use have been devised. This immobilization permits reuse whereas otherwise the enzyme might undergo deactivation or be lost in the reaction medium. The immobilized conjugate may be employed directly in a substrate solution or in a reactor system such as a packed column, depending on the nature of the substrate which is being biocatically reacted.

Several general methods as well as many modifications of the methods have been described in the literature by which immobilization can be effected. For example, materials useful for immobilization of solubilized enzymes or cells containing enzymes are disclosed in U.K. Patent No. 1,444,539. Preferably, the enzymes or cells are treated with a water miscible solvent, such as acetone, dried and then treated with polyethylenimine and glutaraldehyde to make shaped bodies of a water insoluble structure.

Also, in U.S. Pat. No. 4,078,970 there is disclosed the immobilization of glucose isomerase, preferably obtained from cells belonging to the genus, Streptomyces. Release of the intracellular glucose isomerase from the microbial cells is conducted by any of various known processes for disruption of the cells, such as shearing in a blender, autolysis, lysozyme treatment, ultra-sound treatment, pressurized treatment, or detergent treatment. Cell debris is then removed (typically by centrifuging with decantation of the enzyme-containing solution), and the now released glucose isomerase is adsorbed on a macroporous anion exchange resin. The resin is prepared by a known process. For instance, a crosslinkable monomer and a monovinyl monomer are copolymerized in the presence of a material which is removable by a solvent and does not take part in the reaction, such as polystyrene. After polymerization, the resin is treated with solvent to dissolve the polystyrene therefrom. Then, an anion exchange group, such as trimethyl ammonium or dimethyl ammonium, is introduced. For clarity, it is mentioned here that U.S. Pat. No. 4,078,970 uses the term "immobilized" glucose isomerase interchangeably with the term "insolubilized" glucose isomerase to refer to when the glucose isomerase is on the resin support. This should not be confused with the generally accepted terminology in the art of enzyme chemistry to use the term "solubilized" to refer to when an enzyme has been released from the cell and is in solution. Thus, "solubilized" refers to when an extracellular enzyme has been secreted through the cell wall to outside the cell or to when an intracellular enzyme has been brought outside the cell by disruption means such as detergent treatment, sonication, shearing with a blender, and the like.

Similarly, U.S. Pat. Nos. 3,788,945 and 3,960,663 disclose released glucose isomerase (free of cell debris) adsorbed on a porous anion exchange resin such as Amberlite ® IRA 938, Amberlite ® IRA 900 and Amberlite ® IRA 904.

Additionally, in Japanese Kokai Patent No. Sho 51 [1976]-128,474 a glucose isomerase immobilization method which involves the blending of chitosan and glucose isomerase producing bacteria, with subsequent treatment with a polyaldehyde, is disclosed. Immobilization of cells of glucose isomerase producing Streptomyces olivaceus by contacting the cells with glutaraldehyde and a cationic polymer obtained from polymerizing epihalohydrin and an alkylene polyamine to obtain a hard cell aggregate is disclosed in U.S. Pat. No. 4,251,632. On the other hand, immobilization of glucose isomerase producing cells by contacting the cells with glutaraldehyde, a copolymer of epihalohydrin and polyamine, and cellulose or natural gum as binder, and then spheronizing the preparation to obtain a cell aggregate of increased hardness is disclosed in U.S. Pat. No. 4,543,332.

Lastly, a process for depositing and immobilizing various enzymes by causing an aqueous dispersion of the enzyme to flow through an inert, inorganic, porous, sorptive, liquid permeable, metal oxide, supporting matrix is disclosed in U.S. Pat. No. 4,001,085. In the preferred embodiment, the matrix is ceramic and formed by sintering alumina. The porous matrix is enzyme permeable, and the patent discloses a process to deposit the enzyme on the matrix by applying at least 10 psig (1.736 kg/cm$^2$) pressure to cause a dispersion of the enzyme to flow through the matrix. Although this patent discloses many enzymes, it does not mention or suggest immobilization of enzyme-containing cells.

No where in the prior art is there disclosed an active immobilized cell conjugate comprising a strain of enzyme-containing microorganism cells on a macroporous resin, wherein said resin comprises a less expensive, uncharged (non-ionic) resin support. The catalytic activity is not altered as it is when positive or negative charges are present.

STATEMENT OF THE INVENTION

The present invention provides a method for the preparation of an enzyme containing conjugate which comprises: (a) providing an aqueous dispersion of enzyme-containing cells of a microorganism having reactive amine groups as part of its cellular makeup; (b) contacting the dispersion with a macroporous non-ionic resin under reduced pressure to cause the cells to become incorporated into the pores of the resin thereby forming a resin/cell complex; and (c) contacting the resin/cell complex with a multifunctional, amine reactive material thereby to fix the cells and prevent their escape from the pores of the resin. The invention also provides for an immobilized enzyme-containing cell conjugate comprising a macroporous non-ionic resin support having incorporated in the pores thereof the reaction product of an amine reactive material which is a multifunctional aldehyde, a multifunctional organic halide, a multifunctional anhydride, a multifunctional azo compound, a multifunctional isothiocyanate or a multifunctional isocyanate whose amine reactive groups have been reacted with free amine groups of the cells to bind the cells to the amine reactive material. The reaction product of the amine reactive material and the cells comprises an aggregate that is too large to escape from the pores and thus the cells are fixed on the resin.

DETAILED DESCRIPTION OF THE INVENTION

Any macroporous resin may be used in the present invention, provided it is non-ionic (neutral). A neutral resin, as opposed to one carrying a series of positives or negative charges is required because the catalytic activity of the enzyme is not altered as it is when positive or negative charges are present from cationic and anionic resins. By macroporous, is meant that the resin pores are larger than is typical. For instance, the alumina matrix of U.S. Pat. No. 4,001,085, discussed above, is microporous and has an average pore diameter of 0.04 microns. In the present invention, the average pore size is preferably about 80,000 angstroms (about 8 microns) an exponential difference of a factor of $10^2$. In general, the resin employed in the present invention preferably will have a pore diameter preferably in the range of about 25,000 angstroms (about 2.5 microns) to about 230,000 angstroms (about 23 microns). Also, the resin preferably will have a pore depth that is at least about 2 times the average diameter of the cells, and more preferably in a range from about 2 times to about 10 times the average diameter of the cells.

A suitable resin is Amberlite ® XE-238A, a neutral or non-ionic macroporous resin with a polystyrene backbone, supplied by Rohm and Hass, Philadelphia, Pa. Amberlite XE-238A has a particle size in the range of about 20 to 50 mesh on the U.S. series (about 300 to 900 microns), a surface area of about 7 $m^2/g$, and an average pore diameter in the range of about 25,000 angstroms (about 2.5 microns), to about 230,000 angstroms (about 23 microns) with a mean average pore diameter of about 80,000 angstroms (about 8 microns). It is the copolymer precursor to Amberlite ® IRA-938, prior to chloromethylation and aminolysis. Amberlite IRA-938 is a polystyrenedivinylbenzene anion exchange resin with quaternary amine groups, and is present in the chloride form. Also, Amberlite XE-238A is totally hydrophobic, which is believed to help keep the cells from escaping from the resin into the aqueous medium of the substrate during use.

Preferably, the resin is slurried in a solvent, such as water, to facilitate contact with the cells, as described below. The slurry desirably is prepared in a w/v (weight/volume) amount of dry resin beads to water ranging from approximately 0.1 g/100 ml to approximately 60 g/100 ml, more preferably approximately 10 g/100 ml to approximately 45 g/100 ml.

Any enzyme-containing cells of a microorganism having reactive amine groups as part of its cellular makeup may be immobilized on the resin by the method of this invention. Thus, suitable intracellular enzymes include, but are not limited to, yeast lactase from *Sacaromyces serivacae*, invertase from *S. cerivacae*, catalase from *Aspergillus niger*, and glucose oxidase from *A. niger*.

An especially suita le intracellular enzyme is glucose isomerse, as there is considerable interest in the enzymatic conversion of glucose to fructose, especially for the production of fructose-containing syrups from corn starch. Glucose isomerase used for this conversion may be obtained from various microorganisms of genera such as Pseudomonas, Flavobacterium, Arthrobactera, Bacillus, Actinoplanes, and Streptomyces. U.S. Pat. No. 4,283,496 discloses the use of particular strains of an organism of the species *Flavobacterium arborescens*. This patent, however, does not discuss immobilization. The preferred embodiments in the Examples below employ a strain of *F. arborescens* deposit no. ATCC 4358, and glucose isomerase produced by this microorganism. The *F. arborescens* ATCC 4358 may be cultured in a suitable nutrient medium in accordance with the disclosure of U.S. Pat. No. 4,283,496.

After fermentation in a suitable nutrient medium, the enzyme-containing cells are collected, typically by centrifugation followed with decantation, and preferably the collected cells are washed with water. Then, the immobilization is carried out by contacting the resin (or slurry thereof) with a dispersion of the enzyme-containing cells. Usually, this is an aqueous dispersion, although enzyme and resin compatible solvents may be employed. The contact is carried out under a pressure reduced below atmospheric pressure by an amount sufficient to cause diffusion of the water from the resin pores and replacement by the enzyme-containing cell moiety. Preferably, the pressure is reduced from approximately 5 mm of Hg to approximately 100 mm of Hg below atmospheric pressure. In a highly advantageous embodiment, the pressure reduction below atmospheric is in a range of approximately 15 to 20 mm of Hg. The contact is desirably maintained for approximately 10 minutes to 10 hours at approximately 20° C. to 35° C., more preferably approximately 1 to 7 hours at approximately ambient temperature. Contacting the cell dispersion with the resin under reduced pressure causes the cells to become incorporated into the pores of the resin and thereby form a resin/cell complex.

In a preferred embodiment, the microorganism cells containing the intracellular enzyme are at least partially disrupted to release the enzyme prior to contact with the resin. This results in an enzyme system that includes cell fragments, remaining intact cells and solubilized enzyme, all of which have reactive amine groups. It is this system that is contacted with the resin (or slurry thereof) under reduced pressure. Disruption may be accomplished by any of various known means for releasing and thereby solubilizing intracellular enzymes from the cells in which they are contained. One way to accomplish disruption is fractionation with a high speed centrifuge, and several other ways are mentioned above in the "Background" discussion.

Next, the resin/cell complex is treated with a solution of a multifunctional amine reactive material such as glutaraldehyde; bis-diazobenzidine-2,2′-disulfonic acid; 4,4′-difluoro-3,3′-dinitrodiphenylsulfone; diphenyl-4,4-′dithiocyanate-2,2′disulfonic acid; 3-methoxydiphenylmethane-4,4′-diisocyanate; toluene-2-isocyanate-4-isothiocyanate; toluene-2,4-diisothiocyanate; diazobenzidine; diazobenzidine-3,3′-dianisidine; N,N′-hexamethylene bisiodoacetamide; hexamethylene diisocyanate; cyanuric chloride and 1,5-difluoro-2,4-dimitrobenzene by contacting it with a solution of the material preferably containing from about 0.001 to 100 gm per liter of the amine reactive material. A very desirable amine reactive material is a solution that is about 0.5% w/v to about 10% w/v glutaraldehyde in water. After allowing the reaction to proceed for a time sufficient to permit the material to derivatize the free amine groups, the thus treated resin/cell complex is removed from the solution and preferably washed several times with deionized water. As used herein, the term "derivatize" is intended to mean the formation of a reaction product between the amino functional groups of the enzyme-containing cells (or enzyme system) and the amine reactive moiety of the amine reactive material. The amine reactive materials which are water soluble are applied from their aqueous solutions whereas non-water soluble amine reactive materials are applied from organic solvents. It is noted that resins are, in general, soluble in organic solvents. Thus, if the slurry contains a solvent other than water, it must be one that will not appreciably dissolve the resin. Suitable organic solvents are the hydrocarbons such as hexane, cyclohexane, cyclopentane, xylene, benzene, or toluene. Also, the organic solvent will depend on the particular enzyme-containing cells being immobilized, for the chosen solvent must be enzyme compatible. Such compatibility can be easily determined by the person ordinarily skilled in the art without undue experimentation. Contact with the amine reactive material fixes the cells and thus prevents their escape from the resin, as the reaction product of the amine rective material and the cells (or system) comprises an aggregate that is too large to escape from the pores of the resin.

The Examples are intended to illustrate the preferred embodiments of the present invention and not to limit the invention.

EXAMPLE I 4.5 g (grams) of Amberlite ® XE-238A resin beads were slurried in a sufficient amount of water to provide 15 ml (milliliters) of slurry. The 15 ml of Amberlite XE-283A slurry and 15 ml of a slurry of water washed and disrupted cells of bacteria of the species *Flavobacterium arborescens* ATCC 4358 were combined in a 100 ml resrn flask fitted with a vacuum adaptor and subjected to water aspirator reduced atmospheric pressure of approximately 15-20 mm Hg at room temperature with stirring for 6 hours. A resin flask is a 2-piece glass apparatus, the top section of which has 4 separate adapters (ground glass joints) for a stirrer, vacuum attachment, thermometer, and addition funnel. This type of flask was used due to its wide mouth opening, facilitating easy removal of materials from the flask.

The cell-treated Amberlite XE-283A resin, was then filtered through a sieve (80 mesh on the U.S. sieve series, 180 microns). The cell-treated Amberlite XE-238A retained on the sieve was removed and reslurried in a phosphate buffer solution (pH 8.0), placed in a separatory funnel and allowed to settle. After standing for 15 minutes, some resin beads remained at the top; presumably these were beads which had no cells incorporated in them, as Amberlite XE-238A is lighter than water. The beads (Amberlite incorporated with cells) that had settled to the bottom of the funnel were siphoned off, filtered on a Buchner apparatus using Whatman #1 filter paper, washed several times with water and then dried with aspiration on the filter, to provide approximately 3.5 g of cell-treated resin which was scraped from the filter and reslurried in 10 ml of a 0.1% w/v glutaraldehyde in water solution (pH measured at 8.0) with stirring for 1 hour at room temperature. The glutaraldehyde treated cell incorporated resin was then filtered, washed well with water, and air dried overnight to provide 2.2 grams of a cell immobilized conjugate comprising off-white beads.

This product was examined for glucose isomerase activity using the following procedure. A glucose substrate was prepared by mixing 360.32 g of glucose, 4.94 g of $MgSO_4 \cdot 7H_2O$, 0.120 g of $CoCl_2$, and 4.768 g Hepes buffer, made up to 1 liter at pH 8.0. 100 mg of the cell immobilized conjugate was placed in a 125 ml stoppered Erlenmeyer flask containing 50 ml of the glucose substrate solution. The conjugate was allowed to hydrate for 30 minutes at room temperature. Next, the flask was placed in a shaker at 60° C. and agitated for 10 minutes whereupon a 0.1 ml sample was removed and added to 4.0 ml of 0.1M perchloric acid solution as a blank. At 70 minutes, another 0.1 ml sample was removed and added to 4.0 ml of the 0.1M perchloric acid solution. The cysteine-sulfuric acid assay was then run on the two samples. To 0.5 ml of 5% cysteine solution in a $13 \times 100$ mm test tube was added 0.05 ml of the sample. 4.5 ml of 75% sulfuric acid was then added to the mixture, mixed well on a Vortex stirrer, and the tubes placed in a water bath at 37° C. for 30 minutes. The tubes were then removed from the water bath and allowed to cool for 10 minutes. The samples were then read at 412 nm and calculations conducted according to the following equations:

$$\Delta A_{412} = A_{412}(\text{sample}) - A_{412}(\text{blank})$$

$$GIU/g = \frac{\mu \text{ fructose}}{0.05 \text{ ml}} \times \frac{50 \text{ ml substrate}}{0.1 \text{ gm enz.}} \times \frac{1 \mu \text{ mole}}{180.16 \mu \text{gm}} \times$$

$$\frac{4.1 \text{ ml samp. vol.}}{0.1 \text{ ml sample}} \times \frac{1 \text{ hour}}{60 \text{ min.}} = 37.929248 \ \mu\text{g fructose}$$

where $\mu$g fructose=slope (stand curve)$\times \Delta A_{412}$

The activity was found to be 100.9 glucose isomerase units per gram of cell immobilized resin (GIU/g).

EXAMPLE II 4.5 g of Amberlite XE-238A resin beads were slurried in a sufficient amount of water to provide 15 ml, which was then combined with 15 ml of water washed and disrupted cells of bacteria of the species *F. arborescens* ATCC 4358 in a 100 ml resin flask fitted with a vacuum adaptor and subjected to about 15-20 mm Hg water aspirator reduced atmospheric pressure at room temperature with stirring for 6 hours. Then, 0.5 ml of a 10% w/v of glutaraldehyde in $H_2O$ solution was added followed by stirring for 1 hour at room temperature. The resultant cell/resin/glutaraldehyde was filtered through a sieve (80 mesh on the U.S. series), water washed, and air dried to provide 2 grams of cell immobilized conjugate comprising off-white beads. Activity was measured in the same manner as in Example I and found to be 60.7 GIU/g cell immobilized resin. Presumably, the reason this activity is less than that of Example I is due to the absence of the step of reslurrying in phosphate buffer, wherein the beads were allowed to set so that those not incorporated with cells could float to the top and be filtered off. Thus, some of the final product here contains beads without cells and free enzyme incorporated in the pores.

What is claimed is:

1. A method for the preparation of an enzyme containing conjugate which comprises:

(a) providing an aqueous dispersion of enzyme containing cells of a microorganism having reactive amine groups as part of its cellular makeup;

(b) contacting the dispersion with a macroporous non-ionic resin under reduced pressure below atmospheric to cause the cells to become incorporated into the pores of the resin thereby forming a resin/cell complex; and (c) contacting the resin/cell complex with a multifunctional, amine reactive material thereby to fix the cells and prevent their escape from the pores of the resin.

2. The method of claim 1, wherein the resin has an average pore diameter in the range of from about 25,000 angstroms to about 230,000 angstroms.

3. The method of claim 1, wherein the cells are at least partially disrupted.

4. The method of claim 1, wherein the amine reactive material is a multifunctional aldehyde, a multifunctional organic halide, a multifunctional anhydride, a multifunctional azo compound, a multifunctional isothiocyanate or a multifunctional isocyanate.

5. The method of claim 4, wherein the amine reactive material is bis-diazobenzidine-2,2'-disulfonic acid; 4,4'-difluoro-3,3'-dinitrodiphenylsulfone; diphenyl-4,4'-dithiocyanate-2,2'-disulfonic acid; 3-methoxydiphenylmethane-4,4'-diisocyanate; toluene-2-isocyanate-4-isothiocyanate; toluene-2,4-diisothiocyanate; diazobenzidine; diazobenzidine-3,3'-dianisidine; N,N'-hexamethylene bisiodoacetamide; hexamethylene diisocyanate; cyanuric chloride; 1,5-difluoro-2,4-dinitrobenzene; or glutaraldehyde.

6. The method of claim 1, wherein the enzyme is yeast lactase, glucose oxidase, invertase, catalase, or glucose isomerase.

7. The method of claim 6, wherein the enzyme is glucose isomerase which is produced by microorganism cells belonging to the genus Pseudomonas, Flavobacterium, Arthrobacter, Bacillus, Actinoplanes, or Streptomyces.

8. The method of claim 7, wherein the glucose isomerase is produced by microorganism cells belonging to the species *Flavobacterium arborescens*.

9. The method of claim 1, wherein the contacting is accomplished under a pressure reduced below atmospheric pressure by at least about 5 mm of Hg, for about 10 minutes to about 10 hours, at a temperature of about 20° C. to about 35° C.

10. The method of claim 1, wherein the resin has a pore depth in the range from about 2 times to about 10 times the average diameter of the cells.

11. A method of preparing an immobilized enzyme conjugate comprising the steps of:

(a) providing an enzyme system by treating enzyme-containing microorganism cells having reactive amine groups to at least partially disrupt the cells thereby releasing some of the intracellular enzyme therefrom, said system including cell fragments, remaining intact cells, and solubilized enzyme, all of which have reactive amine groups;

(b) contacting the enzyme system with a nonionic, macroporous resin support under a reduced pressure below atmospheric for a sufficient time whereby the intact cells, cell fragments, and solubilized enzyme are incorporated in the pores of the resin to provide a system incorporated resin;

(c) contacting the cell incorporated resin with a solution of multifunctional, amine reactive material to fix the system on the resin whereby there is provided an immobilized cell conjugate.

12. An immobilized enzyme-containing conjugate made by the method of claim 1.

13. A method of preparing an immobilized glucose isomerase conjugate, and converting glucose to fructose therewith, which comprises the steps of:

(a) contacting a macroporous non-ionic resin with a dispersion of glucose isomerase containing cells having reactive amine groups under reduced pressure below atmospheric to cause the cells to be entrapped in the pores of the resin;

(b) removing liquid and any unentrapped cells dispersed therein from contact with the resin and contacting it with a solution of an amine reactive material which is a multifunctional aldehyde, a multifunctional organic halide, a multifunctional anhydride, a multifunctional azo compound, a multifunctional isothiocyanate or a multifunctional isocyanate to cause the amine reactive groups of the amine reactive material to react with the amine groups of the glucose isomerase containing cells;

(c) removing liquid and any unreacted amine reactive material dissolved therein from contact with the resin; and (d) contacting the thus immobilized glucose isomerase with glucose thereby to convert the glucose to fructose.

* * * * *